US006808888B2

(12) United States Patent
Zhang et al.

(10) Patent No.: US 6,808,888 B2
(45) Date of Patent: Oct. 26, 2004

(54) UNIVERSAL NUCLEIC ACID AMPLIFICATION SYSTEM FOR NUCLEIC ACIDS IN A SAMPLE

(75) Inventors: Jing Zhang, St. Louis, MO (US); John Dekker, Beverwijk (NL); Antoinette C. van der Kuyl, Loosdrecht (NL); Jolanda Maas, Amsterdam (NL); Bob van Gemen, Almere (NL)

(73) Assignee: Primagen Holding B.V., Amsterdam (NL)

( * ) Notice: Subject to any disclaimer, the term of this patent is extended or adjusted under 35 U.S.C. 154(b) by 0 days.

(21) Appl. No.: 10/192,786

(22) Filed: Jul. 10, 2002

(65) Prior Publication Data

US 2003/0073112 A1 Apr. 17, 2003

Related U.S. Application Data

(63) Continuation of application No. PCT/NL01/00020, filed on Jan. 15, 2001.

(30) Foreign Application Priority Data

Jan. 13, 2000 (EP) .............................................. 00200109

(51) Int. Cl.$^7$ .......................... C12Q 1/68; C12P 19/34; C07H 19/00; C07H 21/00; C07H 21/04

(52) U.S. Cl. ......................... 435/6; 435/91.1; 435/91.2; 435/7.1; 536/22.1; 536/23.1; 536/24.3; 536/24.31; 536/24.32; 536/24.33

(58) Field of Search ...................... 435/6, 91.2, 91.1, 435/7.1; 536/22.1, 23.1, 24.3, 24.31, 24.32, 24.33

(56) References Cited

U.S. PATENT DOCUMENTS

| 5,104,792 A | 4/1992 | Silver et al. |
| 5,106,727 A | 4/1992 | Hartley et al. |

(List continued on next page.)

FOREIGN PATENT DOCUMENTS

| EP | 0466520 | 1/1992 |
| WO | WO96/15264 | 5/1996 |

(List continued on next page.)

OTHER PUBLICATIONS

McGrath et al., Sequence analysis of DNA randomly amplified from the *Saccharomyces cerevisiae* genome, Molecular and Cellular Probes, 1998, pp. 397–405. vol. 12.

Rose et al., Consensus–degenerate hybrid oligonucleotide primers for amplification of distantly related sequences. Nucleic Acids Research, 1998, pp. 1628–1635, vol. 26, No. 7.

(List continued on next page.)

*Primary Examiner*—Jezia Riley
(74) *Attorney, Agent, or Firm*—TraskBritt

(57) ABSTRACT

Methods for amplifying nucleic acid in a sample comprising providing the sample with a set of primers to enable synthesis of at least one nucleic acid strand complementary to at least part of the nucleic acid, wherein the set of primers comprises between 3–8 random bases, preferably clustered near the 3' end of each primer in said set of primers. The methods of the invention are useful, for example, for determining whether samples derived from humans, mammals, poultry, or fish comprise nucleic acid of a pathogen. The methods are further suited for typing the pathogen and typing particular variants of said pathogen. The methods are also suited for the elucidation of the gene expression profile or genetic profile of cells.

26 Claims, 6 Drawing Sheets

U.S. PATENT DOCUMENTS

| | | | |
|---|---|---|---|
| 5,948,649 A | | 9/1999 | Stewart et al. |
| 6,521,428 B1 | * | 2/2003 | Senapathy ................. 435/91.2 |
| 2001/0021518 A1 | | 9/2001 | Goudsmit et al. |
| 2003/0022194 A1 | * | 1/2003 | Erlander et al. ............... 435/6 |

FOREIGN PATENT DOCUMENTS

| | | | |
|---|---|---|---|
| WO | WO 97 30062 | 8/1997 | |
| WO | WO 98 02575 | 1/1998 | |
| WO | WO 01/51661 A2 | 7/2001 | |
| WO | WO 02/20571 A2 * | 3/2002 | ........... C07K/14/16 |

OTHER PUBLICATIONS

Smith et al, Automated differential display using a flourescently labeled universal primer, Biotechniques, 1997, pp. 274–279, vol. 23, No. 2.

PCT International Search, PCT–NL01 00020, dated Jul. 18, 2002, 2 pages.

PCT International Preliminary Examination Report, PCT NL01 00020, dated Mar. 25, 2003, 2 pages.

* cited by examiner

Microarray/DNA-chip (Prior Art)

SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence

```
<220> FEATURE:
<223> OTHER INFORMATION: Primer JZH2R
<220> FEATURE:
<221> NAME/KEY: misc_feature
<222> LOCATION: (19)..(23)
<223> OTHER INFORMATION: n can be any nucleotide or functional
      equivalent thereof

<400> SEQUENCE: 1
gctatcatca caatggacnn nnng                                              24

<210> SEQ ID NO 2
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(30)
<223> OTHER INFORMATION: n can be any nucleotide or functional
      equivalent thereof
<220> FEATURE:
<221> NAME/KEY: promoter
<222> LOCATION: (1)..(25)
<223> OTHER INFORMATION: T7 promoter sequence

<400> SEQUENCE: 2
aattctaata cgactcacta tagggnnnnn g                                      31

<210> SEQ ID NO 3
<211> LENGTH: 18
<212> TYPE: DNA
<213> ORGANISM: Artificial Sequence
<220> FEATURE:
<223> OTHER INFORMATION: Primer JZH1

<400> SEQUENCE: 3
gctatcatca caatggac                                                     18

<210> SEQ ID NO 4
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n represents 10-30 T residues

<400> SEQUENCE: 4
gctatcatca caatggacn                                                    19

<210> SEQ ID NO 5
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(26)
<223> OTHER INFORMATION: n represents 10-30 T residues
<220> FEATURE:
<221> NAME/KEY: promoter
<222> LOCATION: (1)..(25)
<223> OTHER INFORMATION: T7 promoter sequence
```

```
<400> SEQUENCE: 5
aattctaata cgactcacta tagggn                                                26

<210> SEQ ID NO 6
<211> LENGTH: 73
<212> TYPE: DNA
<213> ORGANISM: Artificial Sequence
<220> FEATURE:
<223> OTHER INFORMATION: Primer GAT01
<220> FEATURE:
<221> NAME/KEY: promoter
<222> LOCATION: (1)..(25)
<223> OTHER INFORMATION: T7 promoter sequence

<400> SEQUENCE: 6
aattctaata cgactcacta tagggagaga aggataccac tagctagcgt tttttttttt        60
tttttttttt ttt                                                            73

<210> SEQ ID NO 7
<211> LENGTH: 50
<212> TYPE: DNA
<213> ORGANISM: Artificial Sequence
<220> FEATURE:
<223> OTHER INFORMATION: Primer GAT02
<220> FEATURE:
<221> NAME/KEY: promoter
<222> LOCATION: (1)..(25)
<223> OTHER INFORMATION: T7 promoter sequence

<400> SEQUENCE: 7
aattctaata cgactcacta tagggagaga aggataccac tagctagcgt                    50
```

UNIVERSAL NUCLEIC ACID AMPLIFICATION SYSTEM FOR NUCLEIC ACIDS IN A SAMPLE

CROSS REFERENCE TO RELATED APPLICATIONS

This application is a continuation of PCT International Application No. PCT/NL01/00020, filed Jan. 15, 2001, designating the United States of America, published in English on Jul. 19, 2001, as International Publication No. WO 01/51661, content thereof being incorporated herein by this reference.

TECHNICAL FIELD

The invention lies in the field of diagnostics. More in particular, the invention lies in the field of molecular diagnostics.

BACKGROUND

The increased knowledge of the molecular basis for disease has generated an increasing demand for more and more sophisticated diagnostic methods that can help identify the exact molecular cause of disease. In particular, for infectious diseases, clinicians want to be able to rapidly identify the pathogen. Importantly, concurrent accurate typing and discrimination of different strains of a pathogen is desired. This is important, for instance, in cases where certain strains have a particular unfavorable phenotype. It is also important, for instance, in the case where the pathogen is capable of rapid mutation of its genome to counteract selective pressures induced by the patient and/or the treatment. One non-limiting example of such a pathogen is, of course, Human Immunodeficiency Virus ("HIV"). HIV is, for instance, capable of evading selective pressure induced by nucleotide analogues through mutation of the reverse transcriptase enzyme. To be able to predict which nucleotide analogue, if any, would benefit the patient, it is desired to know in advance, i.e. before treatment starts, which genotype(s) of HIV prevail in the patient.

One possibility to find the pathogen causing the disease is to harvest a sample from the patient comprising the pathogen and culturing the pathogen on suitable media in the case of a bacterial pathogen or in a suitable marker cell line for a viral and/or mycobacterium pathogen. The pathogen may be typed following and/or during culturing. This culture process can be combined with, for instance, antibiotics and/or other medicines to find the relative resistance/sensitivity of the pathogen to said medicine. This so-called culture driven testing has several advantages and is indeed routinely applied for a number of diseases.

However, generally, the considerable amount of time involved with the culture process necessitates that a treatment schedule be started prior to the identification of the causative agent. This is not desired, since the treatment started may prove to be ineffective. Moreover, for many pathogens, a culture system is as yet not available. Another problem with the culture system is the inherent variability of the procedure. Not all pathogens are equally well cultured outside the body of a patient. In addition, since viability of the pathogen is essential, differences in the handling of the sample outside the body will result in variability of the result. Moreover, the costs involved in the initiation of a screen with the culture system for a wide variety of different possible causative agents in any clinical sample are considerable.

For this reason there is a need for a rapid system for the typing of a pathogen that is versatile, reliable and at least partially able to discriminate between different variants of the pathogen. A number of different strategies have been tried. One such strategy relies on the detection of pathogen-derived nucleic acid in a sample. To be able to rapidly detect such nucleic acid, a nucleic acid amplification step is usually required.

Many nucleic acid amplification methods have been devised that are able to specifically detect a certain pathogen and possibly even a number of different strains of said pathogen. However, such methods usually require the clinician to have at least some idea of the kind of pathogen that may cause the disease in the patient. This is frequently not the case.

BRIEF SUMMARY OF THE INVENTION

The present invention provides a method for detecting, quantifying and/or simultaneous typing of a variety of different nucleic acid sequences in a sample. Preferably, said nucleic acid sequences comprise nucleic acid from a microorganism and/or derivative thereof. The microorganism can be a bacterium, a phage and/or a virus.

Preferably, said microorganism is a pathogenic microorganism. The present invention further allows discrimination between different strains of a microorganism or other sequences. The present invention is not only useful for the typing of a pathogen in a sample of a patient, but it is also applicable for the typing of a pathogen in a sample derived from an animal. Preferably, said animal has a commercial and/or emotional value to a human, such as a pet, a farm animal and/or an animal living in a natural reserve. The invention is also suitable for application in poultry and fish. The method of the invention is, of course, not only suited for the typing and/or detection of a pathogen. The method is generally suited for the typing and/or detection of nucleic acid in a sample. For instance, in the case of cellular DNA or RNA, the method can be used for creating a genetic expression profile, respectively, of the nucleic acid in the sample. Knowing the origin of the nucleic acid in the sample then allows the correlation of the profile with the origin.

In case the origin is nucleic acid of (a specific part of) an individual, the profile, or a part thereof, can be correlated to, for instance, a database of profiles, or parts thereof, of other individuals. Matching of the profile (or part thereof) to known profiles(or parts thereof) allows the correlation of the profile (or part thereof) of the individual with the phenotypes of individuals with matching profiles(or parts thereof) displayed by these other individuals. Thus, the method of the invention can be used generally for the typing and/or detection of nucleic acid in a sample.

In one aspect, the invention provides a method for amplifying nucleic acid in a sample comprising providing said sample with a set of primers comprising between 3 and 8 random bases and at least 8 essentially non-random bases, subjecting said sample to a first nucleic acid amplification reaction, providing said sample with at least one second primer comprising at least 8 bases essentially identical to said non-random bases, subjecting said sample to a second amplification reaction and detecting nucleic acid amplified in said sample. Typically only a limited amplification of nucleic acid will occur in said first nucleic acid amplification reaction. Said first and second amplification reactions are preferably performed separately, optionally including a step to remove any unused primer in said first amplification reaction. This way, the reproducibility of the method is best controlled. However, the first and the second amplification reactions may also be performed simultaneously.

Nucleic acid in said sample may be DNA and/or RNA. A double stranded nucleic acid can be denatured into essentially single stranded nucleic acid prior to the priming of synthesis of a complementary strand of nucleic acid. The complementary strand may be DNA and/or RNA. Synthesis of said complementary nucleic acid is performed under conditions and using enzymes that are known in the art, such as, for instance, conditions and enzymes commonly used for polymerase chain reaction and/or NASBA.

The number of nucleic acids amplified with the method of the invention is dependent on the amount and the complexity of the nucleic acid in the sample. When the complexity, i.e. the number of different sequences in the nucleic acid(s) is low, a small number of nucleic acids will be amplified with the method of the invention. In this case, some nucleic acids will be dominant in the amplificate, resulting in a banding pattern when the amplificate is run on a gel. On the contrary, when the complexity of the nucleic acid in the sample is high, many nucleic acids will be amplified, resulting in a smear when the amplificate is run on a gel. An example of nucleic acid with a particularly low complexity is nucleic acid derived from a small virus and/or plasmid (typically smaller than 10 kb). An example of nucleic acid with a particularly high complexity is cellular DNA (typically comprising >$10^8$ kb). It is clear that the mentioned examples are non-limiting. Many different complexities are possible, and additionally mixtures of low and high complexity nucleic acid can be used for the present invention. However, samples comprising only nucleic acid of low complexity that is smaller than 1 kb are not suited for the present invention. As mentioned above, the number of nucleic acids effectively amplified with the method of the invention is also dependent on the amount of nucleic acid in the sample. When the sample comprises particularly low amounts of nucleic acid, some nucleic acids will be dominant in the amplificate, resulting in a banding pattern when the amplificate is run on a gel. On the other hand, when the amount of nucleic acid in the sample is high, many nucleic acids will be amplified, resulting in a smear when the amplificate is run on a gel.

The dependencies on the complexity and the amount of nucleic acid in the sample are intertwined. For example, when the complexity of the nucleic acid in the sample is high, but the amount of nucleic acid in the sample is low, some nucleic acids will be dominant in the amplificate. As will be discussed in more detail later in the description, amplificates comprising dominant nucleic acids and amplificates comprising many different nucleic acids and amplificates comprising both dominant and many different nucleic acids are useful in the present invention. However, the present invention is only useful when at least two nucleic acids are amplified. Preferably, at least 5 nucleic acids are amplified. More preferably, at least 50 nucleic acids are amplified. Typically, the method is used to amplify approximately 10,000 different nucleic acids, for instance, in samples comprising a relatively large amount of complex nucleic acid.

Although the dependencies mentioned above are intertwined, the person skilled in the art will be able to determine what amount of nucleic acid is required to obtain a specific resulting amplificate.

Preferably, said sample is provided with a set of primers comprising at least three or more different primers. Preferably, said set comprises at least ten different primers.

A nucleotide may be an A, T, C, G, or a U and/or a functional equivalent thereof. A functional equivalent of a nucleotide is any substance capable of mimicking, at least in part, an A, T, C, G, or a U in a nucleic acid. For instance, known nucleotide analogues are suitable substances. Also, substances that can mimic a couple of nucleotides, such as, for instance, inosine are suitable substances. Preferably, said nucleotide analogues allow continued synthesis of the nascent strand.

As used herein, the term "random base" means that between any two primers in said set of primers, there is at least one nucleotide or a functional equivalent thereof at a certain position that is different between the two primers.

Apart from the random bases, primers in said set of primers further comprise an essentially non-random number of bases. This has the advantage that for subsequent amplification and/or detection of synthesized nucleic acid, an essentially known template is provided such that one or more new primers can be devised that can be used for the subsequent amplification and or detection of said synthesized nucleic acid. Preferably, said essentially non-random number of bases comprises between 17 and 22 nucleotides. Subsequent amplification is typically performed with at least one primer comprising a sequence essentially identical to a sequence formed by non-random bases in said at least one primer. There can, of course, be more than one second primer. Furthermore, a second primer can comprise nucleotides in addition, to the nucleotides required to create identity to a non-random sequence of a primer in the first set of primers. Additional nucleotides at the 3' end can be advantageously used in applications wherein additional specificity is required in the amplified product. Additional nucleotides at the 5' end can be advantageously used for the introduction of restriction enzyme sites that can be utilized to clone amplified nucleic acid. Cloning of amplified nucleic acid is often desired when amplified nucleic acid needs to be sequenced.

In the present invention, the number of random bases in the set of primers has been observed to be of crucial importance to the practical application of the method of the invention, for instance, for the detection, quantification and/or typing of nucleic acid in the sample. This is especially crucial to the detection of nucleic acid from a wide variety of different pathogens. When less then 3 random bases are used in the set of primers, the subsequent amplification is not sufficiently versatile to detect a wide variety of different nucleic acids (nucleic acid with different sequences), such as from a wide variety of different microorganisms. Presumably, this is due to a lack of hybridization capability among the various nucleic acids. When more than 8 random bases are used in the set of primers, the signal detected is too specific for particular nucleic acids. When the method is used for the detection of a microorganism, such as a pathogen, this leads to the situation that nucleic acid of the microorganism present in the sample may not be detected with sufficient sensitivity. This is presumably due to the fact that not all possible combinations of 9-mers can be included in a practical way in the amount of primer that can be used in the method of the invention. Without being bound by theory, it is the observation in the present invention that for the capability to detect a wide variety of different nucleic acids, it is necessary to have in the set of primers between 3 and 8 random bases. Preferably, said set of primers comprises between 4 and 7 random bases. More preferably, said set of primers comprises 5 or 6 random bases.

To increase the specificity of the reaction, said random bases are preferably clustered at the 3' end of the primer. In the present invention, it has been observed useful for optimal yield of amplificate to include a G at the extreme 3' end of the oligonucleotides of the set of primers. A set of primers of the invention therefore preferably comprises a G at the extreme 3' end of at least most, and preferably all, of the oligonucleotides contained in the set of primers.

In a preferred embodiment of the invention, the non-random bases in the set of primers comprise a sequence enabling non-nucleic acid-primed nucleic acid synthesis. Such a sequence may be used to obtain further amplification of complementary nucleic acid, which further amplification strengthens the signal obtained from the method of the invention. Moreover, the further amplification may be used in a method tbr determining at least part of a sequence of amplified nucleic acid such that amplified nucleic acid may be typed and/or variants of different nucleic acids, such as different variants and/or strains of a microorganism, may be determined. Preferably the non-nucleic acid-primed nucleic acid synthesis comprises transcription.

In a preferred embodiment, said set of primers comprises the sequence:
5'-GCT ATC ATC ACA ATG GAC NNN NNG-3' (SEQ ID NO:1), and/or
5'-AAT TCT AAT ACG ACT CAC TAT AGG GNN NNN G-3' (SEQ ID NO:2),
wherein N can be any nucleotide or functional equivalent thereof.

For the detection of a wide variety of different nucleic acids, such as from different microorganisms, pathogens and/or different variants of a particular microorganism, it is essential that the amplificate of the amplification reaction be scrutinized. This can be done through detecting the amplificate with a probe specific for amplified nucleic acid, for instance, a probe specific for nucleic acid of a microorganism, such as nucleic acid from a pathogen and/or variant of said pathogen. Alternatively, the amplificate is at least in part sequenced, wherein the resolved sequence is specific for nucleic acid of said pathogen and/or variant of said pathogen.

Sequencing of at least part of the amplificate is particularly favorable when the complexity of the nucleic acid in said sample is relatively small, particularly when said sample comprises essentially one type of nucleic acid, such as nucleic acid from one microorganism. However, sequencing of at least part of the amplificate is also possible when the sample comprises two, three or more types of nucleic acid. In this embodiment of the invention, however, the sample preferably does not comprise more than 5 different types of nucleic acid in a substantial amount. In one embodiment of the invention, it is possible with this method to obtain a complete, or at least nearly complete, sequence of a particular nucleic acid present in said sample. A low complexity of the nucleic acid in the sample can be obtained in various ways, for instance, in applications wherein the nucleic acid of, for instance, a microorganism, preferably a virus and/or a phage, is collected into an enriched fraction. For instance, a sample of cell free serum obtained from an HIV-infected patient will be enriched for nucleic acid of HIV viruses. Such samples, or parts thereof, may be used in a method of the present invention. A sequence of an HIV virus present in said sample can then be determined by sequencing of the amplificate obtained with the method of the invention. Furthermore, sequencing of the amplificate will also enable the typing of at least the dominant HIV variants in the sample.

Alternatively, a sequence may be generated representing a gross average of the various variants of HIV in said sample. For this embodiment of the invention, a sample comprising a low complexity of nucleic acid is preferred. A low complexity of nucleic acid in the sample does not mean that said sample may not contain complex nucleic acid, such as cellular DNA. It can contain complex nucleic acid as long as the amount (by weight) of complex nucleic acid does not exceed the amount (by weight) of said low complexity nucleic acid. Preferably, the amount of complex nucleic acid does not comprise more than 25% of the nucleic acid in the sample. More preferably, the amount of complex nucleic acid does not comprise more than 10% of the nucleic acid in the sample. Of course, it is clear to the person skilled in the art that this feature of the present invention is not only useful for the sequencing and/or typing of different HIV variants, but it is also generally applicable for the typing of nucleic acid in said sample.

In another embodiment of the invention, said detecting of amplified nucleic acid comprises subjecting at least part of said amplified nucleic acid to a hybridization reaction with a multiplicity of nucleic acids preferably present in a microarray and/or DNA-chip and detecting whether amplified nucleic acid hybridized with one or more nucleic acids of said multiplicity of nucleic acids. This embodiment is particularly useful when the complexity of the nucleic acid in the sample is relatively large. This embodiment is also very useful when the type of nucleic acid present in said sample is not known. Preferably, the multiplicity of nucleic acids comprise microorganism nucleic acid or nucleic acid that is a reflection of nucleic acid expressed by a cell. The cell may be any type of cell. When the multiplicity of nucleic acid comprises a reflection of nucleic acid expressed by a cell, it is preferred that the nucleic acid in said sample comprises RNA that is or was expressed by a cell. In such a case, the RNA is preferably first transcribed into DNA with, for instance, a primer capable of recognizing the poly-A tail of mRNA.

The method of the invention can further comprise one or more additional amplification reactions using one or more other primers. Such an additional amplification reaction can be advantageously used to pre-amplify "certain" nucleic acid in the sample. Alternatively, an additional amplification reaction can be used to further amplify at least part of the amplificate of said first and/or second amplification reactions. In this embodiment, therefore, a method of the invention is provided, further comprising an additional nucleic acid amplification of nucleic acid in said sample using at least one primer comprising essentially non-random bases.

In one embodiment, the invention provides a set of oligonucleotides comprising a sequence:
5'-GCT ATC ATC ACA ATG GAC NNN NNG-3' (SEQ ID NO:1), and/or
5'-AAT TCT AAT ACG ACT CAC TAT AGG GNN NNN G-3' (SEQ ID NO:2),
wherein N can be any nucleotide or functional equivalent thereof. In these sets of oligonucleotides, N delineates the position of a random base and C, A, T and G the position of a non-random base.

In another aspect, the invention provides the use of a set of oligonucleotides and/or primers of the invention for the preferred amplification of at least part of a viral nucleic acid. Preferably said set of oligonucleotides and/or primers comprises between 3 to 8 random bases clustered around the 3' end of said oligonucleotides and/or primers and an essentially constant sequence at essentially the 5' end of said oligonucleotides and/or primers for priming the synthesis of a complementary nucleic acid in a nucleic acid amplification method. Typically, said set of oligonucleotides and/or primers provide one or more essentially constant templates for detection and/or further amplification of said complementary nucleic acid. Preferably, said set of primers and/or oligonucleotides comprises a sequence:

5'-GCT ATC ATC ACA ATG GAC NNN NNG-3' (SEQ ID NO:1), and/or

5'-AAT TCT AAT ACG ACT CAC TAT AGG GNN NNN G-3' (SEQ ID NO:2), wherein N can be any nucleotide or functional equivalent thereof. In these sets of oligonucleotides, N delineates the position of a random base and C, A, T and G the position of a non-random base. Preferably, said set of primers provides one essentially constant template for detection and/or further amplification of said complementary nucleic acid.

In yet another aspect, the invention provides the use of a set of primers comprising between 3 and 8 random bases clustered around the 3' end and one or more essentially constant sequences clustered at essentially the 5' end of each primer in said set of primers in a nucleic acid amplification reaction comprising nucleic acid for providing complementary nucleic acid generated with said set of primers in said amplification reaction with one or more tags enabling further amplification and/or detection of said complementary nucleic acid.

In yet another aspect, the invention provides a kit for the amplification of nucleic acid in a sample comprising at least one random primer comprising between 3 and 8 random bases. Preferably, said kit comprises at least one set of oligonucleotides and/or primers of the invention. Preferably, said set of primers and/or oligonucleotides further comprise one or more essentially constant sequences clustered at essentially the 5' end of each primer in said set of primers. Preferably, said nucleic acid in a sample comprises nucleic acid from a microorganism or a derivative thereof.

In yet another aspect, the invention provides the use of a kit of the invention in a method of the invention.

DETAILED DESCRIPTION OF THE INVENTION

Nucleotide sequence analysis has become an important tool in modern molecular biology. Recent technological advancements have enabled high throughput sequencing protocols that generate multiple sequences of 200–800 nucleotides in length. On the most modern systems, 96 of such sequences can be determined simultaneously.

In order to make optimal use of the high throughput capabilities of the modern sequencing methods, a good strategy is important. In particular, sequence analysis of long stretches of nucleotides (>2 kb) and small sample sizes (or a combination of both) is a challenge. In one embodiment, the present invention discloses a method that enables non-specific amplification of nucleic acid in a sample and relative simple sequence analysis of long stretches of nucleotides.

Figure 1:
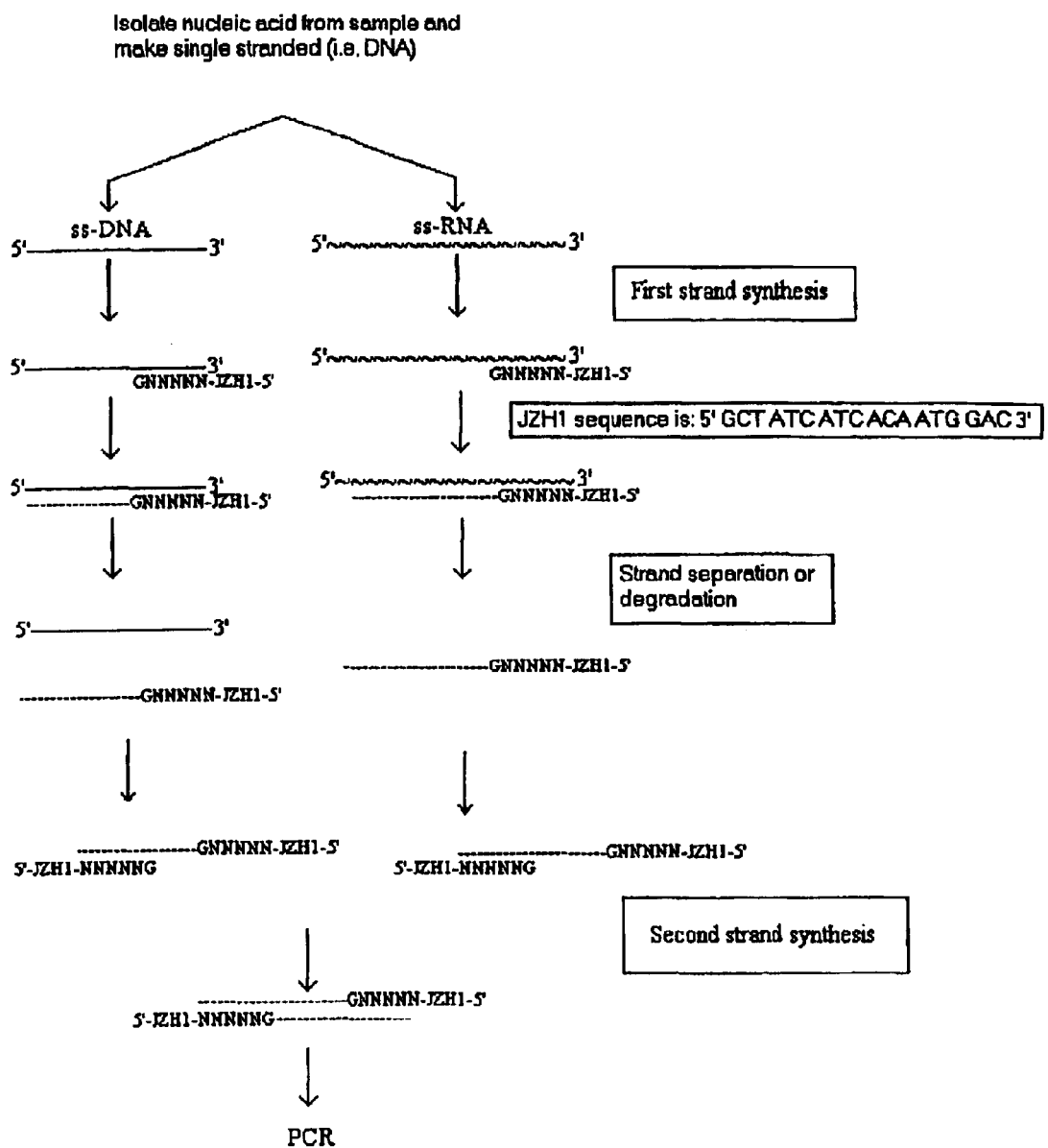
FIG. 1 is a schematic representation of one embodiment of the invention. The primer JZHI corresponds to SEQ ID NO:3

The method consists of a number of steps that can be described as follows:

1) First strand synthesis. The sample nucleic acid is used to copy in a first strand synthesis (i.e. cDNA synthesis) using reverse transcriptase (if RNA or DNA is the nucleic acid being sequenced) or DNA-dependent DNA polymerase (if DNA is the nucleic acid being sequenced), see FIG. 1. The oligos that are used to prime the first strand synthesis consist of a specific sequence at the 5' part of the oligo and a random sequence at the 3' part of the oligo. An example of such an oligo is JZH2R, which has the following sequence: 5'-GCT ATC ATC ACA ATG GAC NNN NNG-3' (SEQ ID NO:1). Typical of JZH2R (SEQ ID NO:1) is that the oligo has a G residue at its 3' end flanking the random sequence. The length of the cDNA will vary depending on the exact location where the random part of the oligo was hybridized and the length of the elongation by the polymerase.

2) Stand separation or degradation. Following the first strand synthesis, the newly made DNA strand is separated from its template strand by denaturation or by degradation of the template strand with RNase H in case the template strand was RNA, see FIG. 1.

3) Second strand synthesis. Using oligo JZH2R (SEQ ID NO:1) in combination with a DNA-dependent DNA polymerase, a second DNA strand is synthesized complementary to the first strand synthesized (i.e. the cDNA), see FIG. 1.

4) PCR amplification. The newly formed double stranded DNA molecules of variable length are amplified by PCR using an oligo primer that fits the specific part of the oligo that was used in the first and second strand protocol described above. In the case of JZH2R (SEQ ID NO:1), that oligo primer would be 5'-GCT ATC ATC ACA ATG GAC-3' (SEQ ID NO:3), which is named JZH1, see FIG. 1.

5) Cloning and sequencing. The PCR fragments that display a wide variety in length are cloned into a plasmid and used for transformation of E. coli cells using standard protocols known by persons skilled in the art. After growing individual colonies overnight, the plasmids of the individual colonies are isolated and used for sequence analysis of both strands of the DNA, obtaining a sequence of 400–1000 nucleotides per clone.

In addition, the above mentioned method can be used for non-biased amplification of all RNAs or DNA from a sample from a small amount to amounts sufficient for analysis of labeling.

With the incorporation of an RNA polymerase promoter sequence instead of the specific sequence part of the primers, the method can be coupled to a transcription reaction. An example of such a primer would be: 5'-AAT TCT AAT ACG ACT CAC TAT AGG GNN NNN G-3' (SEQ ID NO:2) containing a T7 RNA polymerase promoter sequence. Following the PCR step (see flow chart in FIG. 1) a transcription reaction can be performed using T7 RNA polymerase translating the PCR fragments into RNA. Approximately 100–1000 copies of RNA are made per DNA template in a transcription reaction with T7 RNA polymerase. During the transcription reaction, the RNA may be labeled, enabling subsequent analysis of the RNA, for instance, via hybridization on a microarray or DNA-chip.

In another embodiment, the method can be used for the non-biased amplification of mRNA. In that case, the first strand cDNA synthesis will be performed with an oligo that consists of a poly-T stretch (10 to 30 T residues) at the 3' end and a specific sequence at the 5' end (e.g., 5'-GCT ATC ATC ACA ATG GAC $T_{(10-30)}$-3' (SEQ ID NO:4)). For the second strand synthesis, an oligo with a random sequence can be used, e.g. JZH2R (5'-GCT ATC ATC ACA ATG GAC NNN NNG-3' (SEQ ID NO:1)). Following the second strand synthesis, the double stranded DNA can be amplified with a PCR or other nucleic acid amplification reaction (e.g., NASBA, TMA, rolling circle amplification).

In another embodiment, the method used for the non-biased amplification of mRNA described above may be coupled to a transcription reaction by incorporation of an RNA polymerase promoter sequence in the primer used for the first strand synthesis. An example of such a primer would be: 5'-AAT TCT AAT ACG ACT CAC TAT AGG $GT_{(10-30)}$-3' (SEQ ID NO:5). Following the second strand synthesis, the double stranded DNA can be used as a template in a PCR amplification, and the amplified PCR fragments can be used as templates in a transcription reaction with T7 RNA polymerase in case the primer described above is used that contains the T7 RNA polymerase promoter sequence. Following the second strand synthesis, the double stranded DNA can also be directly used as a template in a transcription reaction with T7 RNA polymerase in case the primer described above is used that contains the T7 RNA polymerase promoter sequence.

During the transcription reactions, the RNA that is made can be labeled with a detectable moiety, e.g., a radioactive or fluorescent label. Subsequently, the RNA can be used for analysis on microarrays or DNA-chips, for instance, to elucidate the expression profile of the cells in the sample that the RNA was isolated from.

EXAMPLES

Materials and Ingredients

All basic ingredients for buffers TRIS™, MgCl$_2$, KCl. etc.) were purchased from Merck Nederland BV. Postbox 8198,1005 AD Amsterdam, The Netherlands, or Sigma-Aldrich Chemie BV, Stationsplein. Postbox 27,3330 AA Zwijndrecht, The Netherlands. RNasin, MMLV reverse transcriptase and AMPLITAO™ DNA polymerase were purchased from PE Applied Biosystems, Benelux, Hoogeveenenweg 100, Postbox 305,2910 AH Nieuwerkerk a/d Ussel, The Netherlands. RNase H was purchased from Roche Diagnostics Nederland BV, Post Box 1007,1300 BA Almere. The Netherlands. SEQUENASE™ DNA polymerase and dNTPs were purchased from Amersham Pharmacia Biotech, 800 Centennial Avenue. P0 Box 1327, Piscataway, N.J. 08855, USA. The TOPO-TA™ cloning kit (containing the pCR2.1-TOPO plasmid vector) was purchased from Invitrogen BV, Dc Schelp 12,9351 NV Leek, The Netherlands. Oligonucleotides were purchased from different oligonucleotide suppliers and were usually purified by the supplier and tested for functionality in a PCR reaction with a known amount of input. Sequence analysis was-preformed using the ABI Prism kits purchased from PE Applied Biosystems, Benelux, Hoogeveenenweg 100, Postbox 305,2910 AH Nieuwerkerk a/d lissel, The Netherlands.

Input for a method of the invention is purified nucleic acid that can be isolated from (clinical) samples by a wide variety of methods. One of the methods that is very suitable for this purpose is the method described in Boom R, Sol C J, Salimans M M, Jansen C L, Wertheim-van Dillen P M, van der Noordaa J (1990), "Rapid and simple method for purification of nucleic acids," *J. Clin. Microbiology* 28(3): 495–503.

Example 1

In this example, we compared different primers to amplify MS2-phage RNA. Four different primers were tested (see Table 1). After isolation and purification, $4.0\times10^9$, $4.0\times10^7$, $4.0\times10^5$, $4.0\times10^3$ and $4.0\times10$ copies of MS-2 phage RNA were used as input to do this experiment.

TABLE 1

| \multicolumn{2}{c}{Primers used in this example} ||
| Name | Sequence |
| --- | --- |
| JZH2R | 5'-GCT ATC ATC ACA ATG GAC NNN NNG-3' (SEQ ID NO:1) |
| JZH1 | 5'-GCT ATC ATC ACA ATG GAC-3' (SEQ ID NO:3) |

The experiment was performed using 10 μl of MS2 phage RNA at the amounts mentioned above. The RNA was heated 5 minutes to 80° C. and subsequently cooled on ice to denature any double stranded nucleic acid and structures in the RNA. Subsequently, 10 μl of mixture A (100 mM KCl, 20 mM Tris, pH=8.3, 10 mM MgCl$_2$, 2 μM dATP, 2 μM dTTP, 2 μM dCTP, 2 μM dGTP, 50 ng primer (see Table 1), 0.5 μl RNasin and 25 units MMLV reverse transcriptase) was added to the RNA and incubated for 10 minutes at ambient temperature, followed by an incubation at 42° C. for 30 minutes. Subsequently, the reaction was incubated at 80° C. for 5 minutes and cooled down to ambient temperature, followed by the addition of 0.5 μl RNase H (0.5 units) and further incubation at 37° C. for 30 minutes. After this incubation, the reactions are placed on ice to stop the reaction of RNase H.

The second strand synthesis was performed by using 20 μl of the first strand synthesis (on ice) and adding 20 μl of mixture B (70 mM Tris, pH=7.5, 50 mM NaCl, 35 mM MgCl$_2$, 2 μM dATP, 2 μM dTTP, 2 μM dCTP, 2 μM dGTP, 100 ng primer with random sequence (see Table 1), and 2.6 units Sequenase DNA polymerase) and incubating on ice for 10 minutes, subsequently incubating at ambient temperature for 10 minutes, followed by incubation at 37° C. for 30 minutes. After the reaction, the tubes are placed on ice and 2 µl is used for subsequent PCR amplification.

The PCR reactions were performed by adding to the 2 µl second strand synthesis reactions 48 µl PCR mix (50 mM Tris, pH=8.3, 20 mM KCl, 0.1 mg/ml BSA, 1.8 mM MgCl$_2$, 0.1 µM dATP, 0.1 µM dTTP, 0.1 µM dCTP, 0.1 µM dGTP, 100 ng PCR primer (see Table 1)) and incubating at 95° C. for 5 minutes, followed by 45 cycles of 20 seconds at 95° C., 30 seconds at 55° C., and 2 minutes 72° C. Following the last cycle, the reactions are incubated for 10 minutes at 72° C., subsequently 10 minutes at 40° C., and stored at 4° C. or −20° C. until further use.

In the PCR reactions, primer JZH1 (SEQ ID NO:3) was used for PCR amplification of reactions that were made with primer JZH2R (SEQ ID NO:1). In every experiment H$_2$O was used as a negative control.

Figure 2:
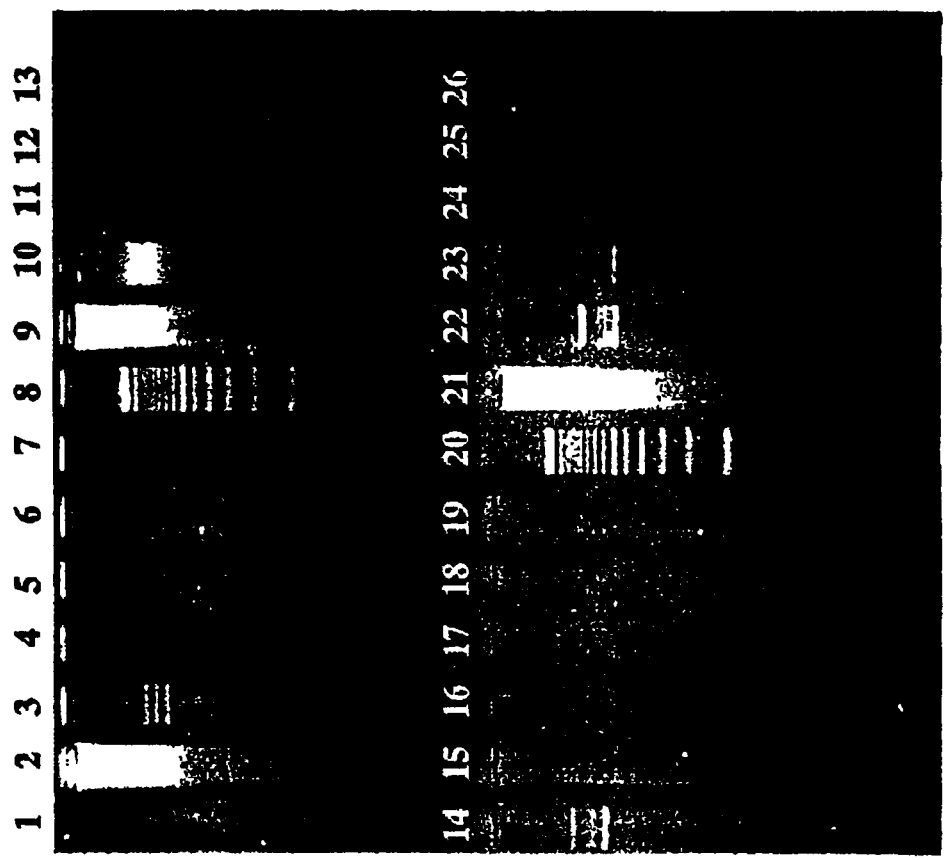
FIG. 2 is an ethidium bromide-stained agarose gel showing the amplification products of the PCR reaction: Lanes 2–7: reactions performed with primer TAG7 (N6); Lanes 9–13: reactions performed with primer TAG7 (N5G); Lanes 14–19: reactions performed with primer TAG20; Lanes 21–26: reactions performed with primer JZH2R (SEQ ID NO:1); Lanes 8 and 20 are markers. Input concentration of $4.0 \times 10^9$ MS2 RNA copies was used for reactions loaded in lanes 2, 9, 14 and 21. Input concentration of $4.0 \times 10^7$ MS2 RNA copies was used for reactions loaded in lanes 3, 10, 15 and 22. Input concentration of $4.0 \times 10^5$ MS2 RNA copies was used for reactions loaded in lanes 4, 11, 16 and 23. Input concentration of $4.0 \times 10^3$ MS2 RNA copies was used for reactions loaded in lanes 5, 12, 17 and 24. Input concentration of 40 MS2 RNA copies was used for reactions loaded in lanes 6, 13, 18 and 25. Negative control reactions are shown in lanes 7, 19 and 26.

Of each PCR reaction, 15 µl was run on an agarose gel and stained with ethidium bromide (standard protocols known to persons skilled in the art), the results of which are depicted in FIG. 2.

From the data in FIG. 2 it is clear that the JZH2R (SEQ ID NO:1) gives the best results with products visible on the agarose gel after PCR amplification when the method was started with only 4.0×10$^5$ copies of MS2 phage RNA. Furthermore this example shows the applicability of the method to analyze RNA sequences.

Example 2

In this example we show the ability of a method of the invention to analyze DNA sequences. A Hepatitis B virus (HBV)-positive serum was used as input to do this experiment. Nucleic acid isolated and purified from the serum were subjected to DNase I and RNase A treatment, respectively, to show the difference in analysis when either the DNA or RNA had been degraded. As a control, a non-treated serum sample was analyzed. In addition to direct analysis of a serum sample, the same set of experiments were done on the supernatants of a serum sample that was briefly centrifuged (10 minutes at 3,000 g) to remove any cellular debris in the serum sample.

The method used in this example was identical to the method used in Example 1, with the following minor changes: (1) no RNasin was used for the analysis of DNA samples; (2) in the case of a DNA template, a DNA-dependent DNA polymerase may also be used instead of the reverse transcriptase for the first strand synthesis; in this particular experiment, reverse transcriptase was used; and (3) the second strand synthesis was amplified 10 times in 10 independent PCR reactions.

Figure 3:
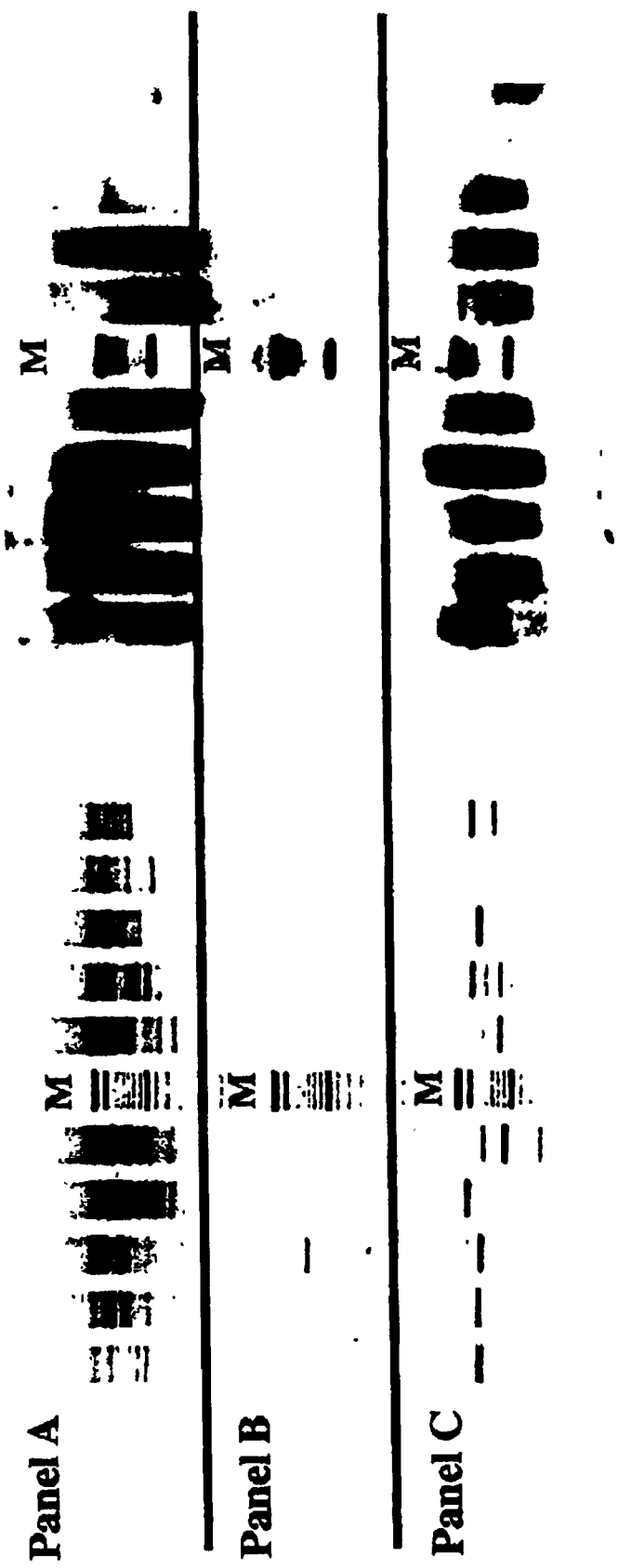
FIG. 3 is an ethidium bromide-stained agarose gel (left half) and HBV DIG-labeled probe hybridized blot (right half) of the 10 independent PCR reactions per second strand synthesis in this example. Panel A: non-treated serum; Panel B: DNase I-treated serum; Panel C: RNase A-treated serum. Lanes marked with M are marker lanes.

The results are depicted in FIG. 3. The PCR fragments (see flowchart in FIG. 1) were analyzed on an agarose gel and visualized with ethidium, bromide. Subsequently, the bands from the gel were transferred to a filter with a standard blotting procedure known to persons skilled in the art. The bands on the filter were interrogated (i.e. hybridized) with a specific digoxygenin (DIG)-labeled probe covering the whole HBV genome of 3 kb (see FIG. 3).

The results clearly show that without any treatment of the serum sample (Panel A in FIG. 3) the most bands in the 10 independent PCR reactions are observed. DNase treatment decreases the number of bands to virtually zero (Panel B in FIG. 3), while RNase treatment still enables the amplification of some bands (Panel C in FIG. 3). The DNase I-treated nucleic acids contained no HBV positive bands (Panel 3, the right half of FIG. 3), while the RNase A-treated nucleic acids still contained HBV positive bands confirmed by hybridization with DIG-labeled HBV probe bands (Panel C, the right half of FIG. 3). This result demonstrates that this method can randomly amplify not only RNA, as in Example 1, but also DNA.

Example 3

In this example, the serum of a patient suspected of infection with HIV-1 (antibody positive for HIV-1), HHV8, HBV and HGV was analyzed with a method of the invention. Nucleic acid was isolated and purified from 100 µl serum of this patient, and 10 µl and 30 µl of nucleic acid solution (total 100 µl) was used for two independent experiments (the protocol as described in Example 1 was applied). Per second strand synthesis (see flow chart in FIG. 1), 10 PCR reactions were performed. The PCR fragments were cloned in the TOPO-TA plasmid vector according to the manufacturer's instructions (Invitrogen BV, De Schelp 12, 9351 NV Leek, The Netherlands). After transformation of E. coli cells, a total of 198 different inserts in the plasmid were sequenced, and of the 198 sequences, 2 sequences were from HBV and 2 sequences were from HGV. The remaining 194 sequences were all of human origin or unknown (i.e. no homology found in the GenBank and EMBL nucleic acid databases). These results show that the method of the invention is capable of simultaneously analyzing both DNA (HBV genome) and RNA (HGV genome) sequences. The probable reason for not finding any HIV-1 or HHV8 sequences in the analysis in this example is most likely the low number of copies of the HIV-1 and HHV8 viruses in the sample used for the analysis.

Example 4

The same serum sample as used in Example 3 was used in this example. We used 0.5 ml of serum to load on a 10 ml continuous sucrose gradient (10% to 60% sucrose w/v), which was centrifuged for 18 hours at 30,000 rpm at 4° C. in a Beckman SW41Ti swing-out rotor in a Beckman ultracentrifuge. After the centrifugation, 0.25 ml fractions were collected from the bottom of the tube. The density of the sucrose solution in each fraction was determined using a refractometer, and each fraction was tested for the presence of HBV virus particles by an HBV-specific PCR reaction detection HBV DNA. The HBV DNA peak was found in fractions with a density of 1.186 g/ml to 1.205 g/ml. This peak fraction was pooled and nucleic acid isolated and purified. The nucleic acid was analyzed using the method as described in Example 1. After the PCR reactions, 14 different discrete bands were cloned in the TOPO-TA plasmid vector according to the manufacturer's instructions (Invitrogen BV, De Schelp 12,9351 NV Leek, The Netherlands) and sequenced. All 14 inserts in the plasmid were HBV sequences, and together they covered 2.8 kb of the HBV genome that is in total 3.2 kb.

Figure 4:
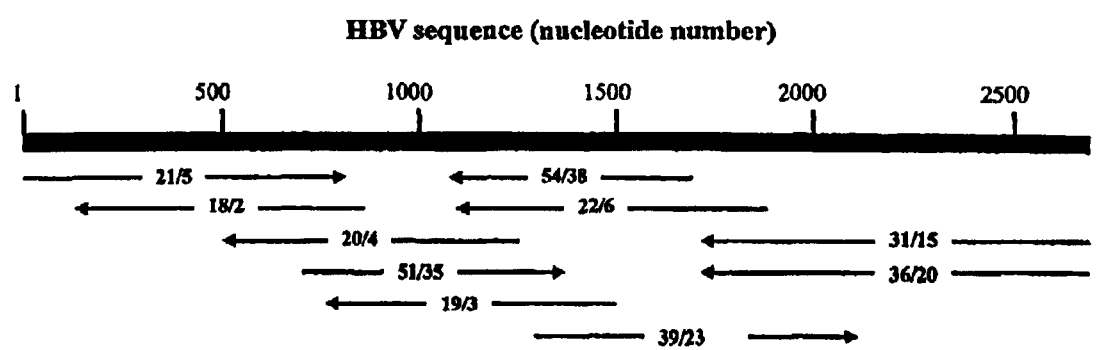
FIG. 4 is a schematic presentation of the sequences obtained in this example (the arrows) on the HBV genome sequence (the red filled bar). The numbers in each arrow represent the lane number on the sequence gel (left of the slash) and the number of the clone (right of the slash).

A schematic presentation of the location of part of the sequences on the HBV genome is shown in FIG. 4. The data clearly show the applicability of the methods of the invention to obtain the nucleotide sequence of a long genome in a homogenous solution. The same method can, of course, be applied to the sequence analysis of long inserts in cloning systems like plasmids, phage lambda or yeast systems. The methods of the invention are very suitable, for instance, to determine the nucleotide sequences of inserts larger than 10 kb in phage lambda.

Example 5

The experiment in this example was performed with the protocol as described in Example 1. The input material for the first strand synthesis was nucleic acid isolated from the culture supernatant of an HIV-1 culture. The primer that was used for the first strand synthesis was primer JZH2R (5'-GCT ATC ATC ACA ATG GAC NNN NNG-3' (SEQ ID NO:1)). After the second strand synthesis (see Example 1), the products were diluted in water and the serial dilutions used as input for the PCR amplification reaction. The PCR reaction (see Example 1) was performed with primer JZH1 (5'-GCT ATC ATC ACA ATG GAC-3' (SEQ ID NO:3)). Dilutions of 10, 100, 1,000, 10,000 and 100,000 times of the second strand synthesis were used for amplification.

Figure 5:
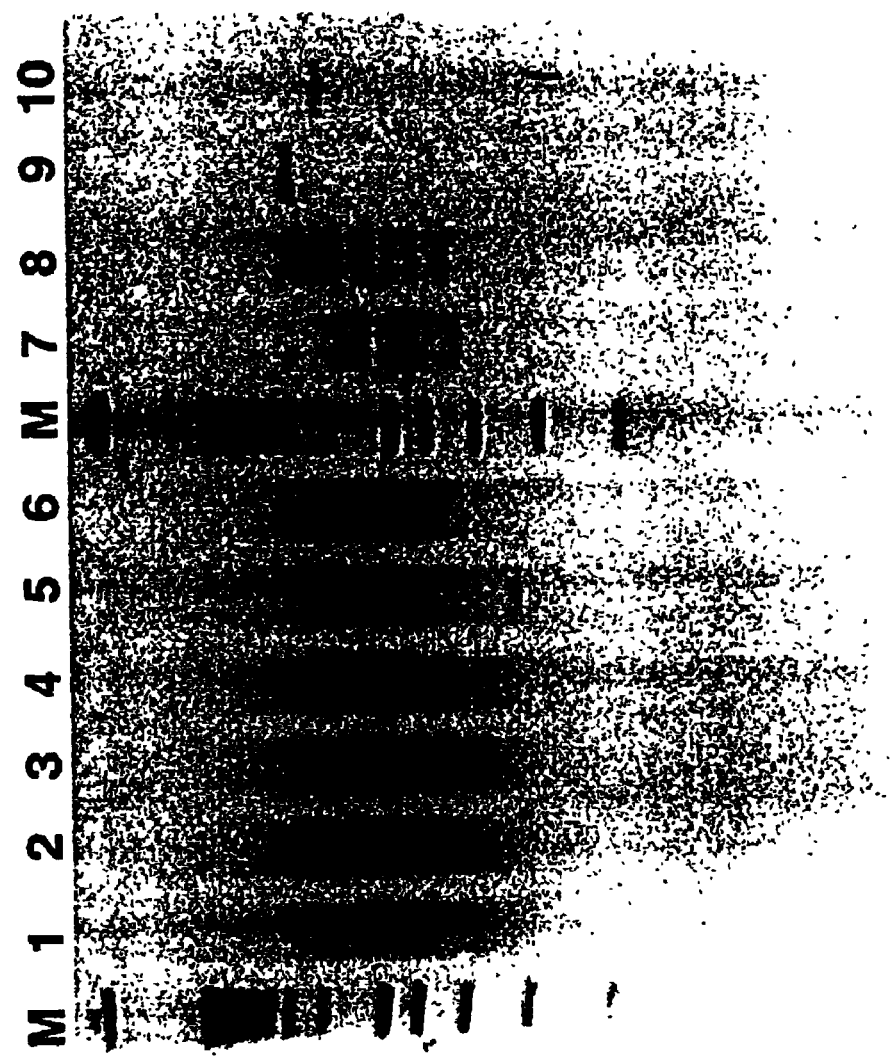
FIG. 5 is an ethidium bromide-stained agarose gel of the amplification results using a dilution of the second strand cDNA synthesis as input for the PCR amplification. Lanes 1–2 is 10-fold dilution, lanes 3–4 is 100-fold dilution, lanes 5–6 is 1,000-fold dilution lanes 7–8 is 10,000-fold dilution, and lanes 9–10 is 100,000-fold dilution.
Figure 6:
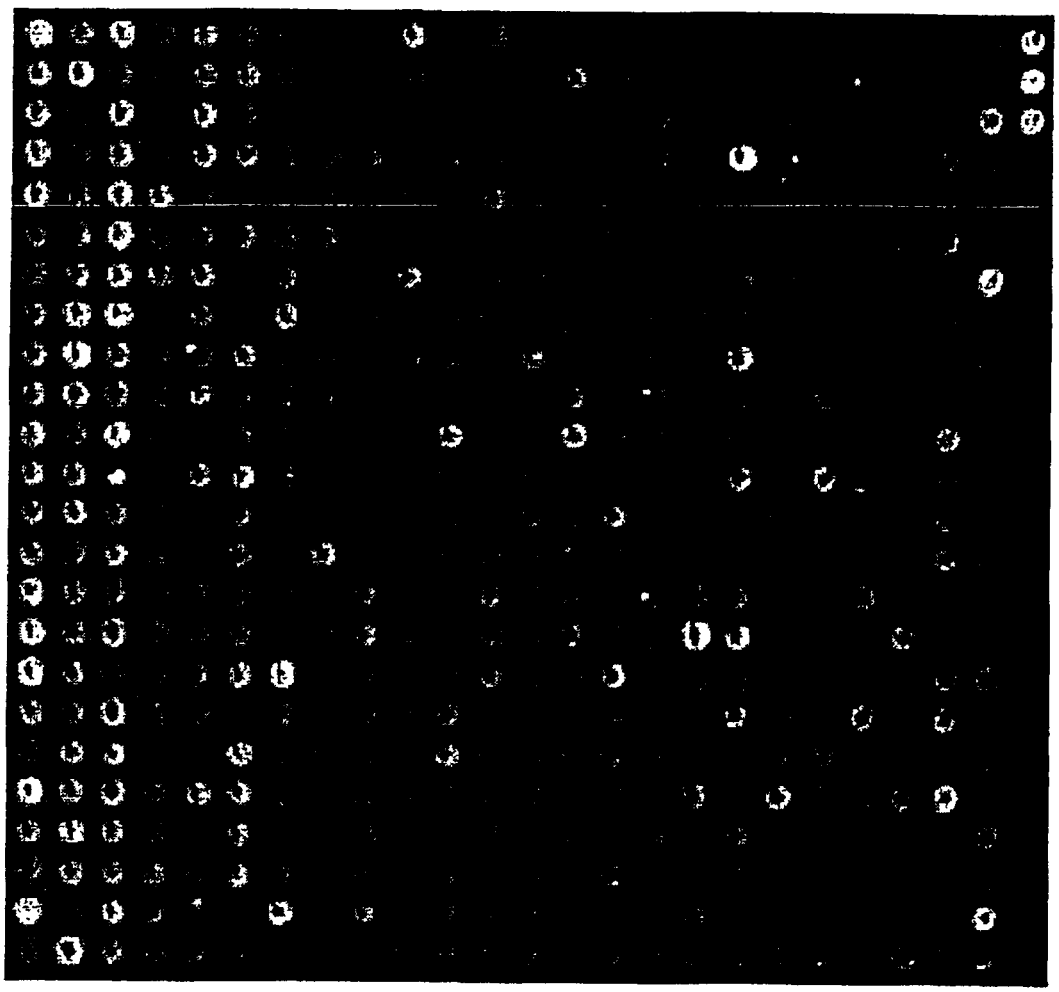
FIG. 6 depicts a conventional microarray and/or DNA-chip.

The results are shown in FIG. 5. The results clearly show that input with a high complexity (i.e. many different sequences) will result in a smear of products after the amplification, illustrating the non-biased nature of the amplification. The complexity of sequences consists of cellular and viral sequences in the culture supernatant that is the result of cell lysis and non-adherent cells in the culture.

When the complexity of the input sequences is decreased by dilution, the chances for a particular sequence to be part of the pool decreases, and not all sequences are represented in the input material. Furthermore, the decrease in absolute copy number of the target sequences also allows only a few amplicons per target sequence to be made. Both of these phenomena result in only a few bands per amplification (lanes 7–10). After cloning, these bands are suited for sequence analysis, for instance, of the HIV-1 genome. If the bands also contain human cellular sequences, it may be necessary to purify the viral particles before application of the GAT procedure if the goal is sequence analysis of the HIV-1 genome. Such purification can be achieved by spinning down of cells and removal of background nucleic acid by DNase and RNase treatment prior to nucleic acid isolation. Dilution of the nucleic acid after second strand synthesis would then cause a few (10–100) bands to be the result of the amplification. These bands can then be sequenced, showing the HIV-1 genomic sequence.

Example 6

First strand synthesis is performed as described in Example 1 using total poly-A mRNA isolated from cells as the input for the first strand synthesis (1–5 mg). The primer used for the first strand synthesis is GAT01 (5'-AAT TCT AAT ACG ACT CAC TAT AGG GAG AGA AGG ATA CCA CTA GCT AGC GTT TTT TTT TTT TTT TTT TTT TTT T-3' (SEQ ID NO:6), the T7 promoter sequence is shown in italics). The second strand synthesis is performed as described in Example 1 using primer JZH2R (5'-GCT ATC ATC ACA ATG GAC NNN NNG-3' (SEQ ID NO:1)).

The second-strand synthesis (or part thereof) is used as input for amplification in a NASBA reaction. The NASBA reaction (Tris-HCl 40 mM, pH=8.5, MgCl$_2$ 12 mM, KCl 70 mM, DTT 5 mM, dNTPs (each) 1 mM, rATP 2 mM, rUTP 2 mM, rCTP 2 mM, rGTP 1.5 mM, ITP 0.5 mM, EDTA 0.75 mM, DMSO 15% v/v, oligonucleotide P1 (GAT02: 5'-AAT TCT AAT ACG ACT CAC TAT AGG GAG AGA AGG ATA CCA CTA GCT AGC GT-3' (SEQ ID NO:7)) 0.2 μM, oligonucleotide P2 (JZHI: 5'-GCT ATC ATC ACA ATG GAC-3' (SEQ ID NO:3)) 0.2 μM, and Sorbitol 0.375 M) was incubated at 65° C. for 5 minutes and subsequently at 41° C. for 5 minutes. Then the enzyme mix was added (BSA 2.1 mg, RNase H 0.01 units, T7 RNA Polymerase 37 units, AMV-RT 7.5 units) and after gentle mixing by tapping the reactions were incubated at 41° C. in a water bath for 90 minutes.

The analysis of the amplification on an ethidium bromide-stained agarose gel shows smears, indicating the non-biased amplification of all poly-A mRNAs present in the input sample.

Example 7

The experiment in this example was performed with the protocol as described in Example 1. The input material for the first strand synthesis was poly-A+mRNA provided as a control by CLONTECH array systems. The amount of poly-A+mRNA used in subsequent reactions with diluted nucleic acid was equivalent to the amount of poly-A+mRNA present in 10,000, 1000, 100. 10 or 1 cell(s). First and second strand syntheses were performed as described in Example 1. The complete cDNA product was subsequently used as input for the PCR amplification reaction. The PCR reaction (seer Example 1) was performed with primer JZHI (5'GCT ATC ATC ACA ATO GAC-3'(SEQ ID NO:3)), and after the amplification step, the amplification products were purified using a NUCLEOSPIN™ column, supplied with arrays (CLONTECH Inc., 1020 East Meadow Circle, Palo Alto, Calif. 94303, USA, Subsequently, the amplification products were radiolabeled with alfa-32P-dATP in a primer extension reaction with random hexamers or a collection of specific oligonucleotides supplied with the ATLAS array's (CLONTECH Inc.

The labeled products of the amplification were hybridized onto an ATLAS mouse array filter containing probes for approximately 600 genes of the mouse genome (CLONTECH Inc., 1020 East Meadow Circle, Palo Alto, Calif. 94303, USA, www.clontech.com). Hybridizations were performed according to the protocol CLONTECH supplies with the ATLAS arrays.

Results

All dilutions of the poly-A+ mRNA gave smears on gels, indicating the generic, non-biased amplification of all mRNAs in the sample. After hybridization of the amplified products generated with a poly-A+ mRNA input equivalent to 1000 cells, approximately 70 genes lighted up on the autoradiograph with some clear differences in the expression level of the genes. This result clearly shows the suitability of the GAT method described in this invention for preparing mRNA for analysis on (micro) arrays.

What is claimed is:

1. A method for amplifying nucleic acids in a sample, said method comprising:
    providing said sample with a first set of primers, each member of said first set of primers comprising between 3 and 8 random bases and at least 8 essentially non-random bases;
    subjecting said sample to a first nucleic acid amplification reaction;
    providing said sample with at least one second primer comprising at least 8 bases essentially identical to said at least 8 essentially non-random bases;
    subjecting said sample to a second amplification reaction; and
    detecting amplified nucleic acid in said sample.

2. The method according to claim 1, wherein said first set of primers has between 17 and 22 essentially non-random bases.

3. The method according to claim 1, wherein said first set of primers has between 4 and 7 random bases.

4. The method according to claim 1, wherein said first set of primers has 5 or 6 random bases.

5. The method according to claim 1, wherein said random bases are clustered at the 3' end of each member of said first set of primers.

6. The method according to claim 1, wherein each member of said first set of primers comprises a G at the 3' end.

7. The method according to claim 1, wherein said at least 8 essentially non-random bases comprise a sequence enabling non-nucleic acid-primed nucleic acid synthesis.

8. The method according to claim 7, wherein said non-nucleic acid-primed nucleic acid synthesis comprises transcription.

9. The method according to claim 1, wherein said set of primers comprises SEQ ID NO:1.

10. The method according to claim 1, wherein said detecting amplified nucleic acid comprises determining the sequence of at least part of said amplified nucleic acid.

11. The method according to claim 1, wherein the detection of amplified nucleic acid comprises:
    subjecting at least part of said amplified nucleic acid to a hybridization reaction with a plurality of nucleic acids; and
    detecting whether said amplified nucleic acid hybridizes with one or more of said plurality of nucleic acids.

12. The method according to claim 11, wherein said plurality of nucleic acids is present in a microarray or DNA-chip.

13. The method according to claim 1, further comprising subjecting said sample to a third amplification reaction using at least one third primer comprising essentially non-random bases.

14. A set of oligonucleotides, said set of oligonucleotides comprising at least one of SEQ ID NO:1 and SEQ ID NO:2.

15. A method for preferentially amplifying at least part of a viral nucleic acid, said method comprising:
    providing a sample comprising said viral nucleic acid;
    providing said sample with a set of oligonucleotides comprising SEQ ID NO:1;
    subjecting said sample to a nucleic acid amplification reaction; and
    detecting amplified viral nucleic acid in said sample.

16. A nucleic acid amplification reaction of the type providing one or more primers with a nucleic acid sequence enabling further amplification and/or detection of complementary nucleic acid generated in said nucleic acid amplification reaction, wherein the improvement comprises using a set of primers, each member of said set of primers comprising between 3 and 8 random bases clustered around the 3' end and one or more essentially constant sequences clustered at essentially the 5' ends.

17. The nucleic acid amplification reaction of claim 16, wherein said set of primers provides an essentially constant template for detection and/or further amplification of said complementary nucleic acid.

18. A kit of parts for implementing a nucleic acid amplification reaction on a sample comprising nucleic acid, said kit of parts comprising:
   a set of primers comprising between 3 and 8 random bases, at least 8 essentially non-random bases, and at least one second primer comprising at least 8 bases essentially identical to said at least 8 essentially non-random bases.

19. The kit of parts of claim 18, further comprising:
   means for implementing a nucleic acid amplification reaction on said sample using said set of primers.

20. The kit of parts of claim 18, wherein said nucleic acid comprises nucleic acid from a microorganism.

21. A kit of parts for implementing a nucleic acid amplification reaction on a sample comprising nucleic acid, said kit of parts comprising:
   a set of primers comprising between 3 and 8 random bases, wherein said set of primers comprises SEQ ID NO:1.

22. A method for producing a positive or a negative diagnosis of pathogenic infection in a subject, comprising:
   obtaining a sample from the subject;
   providing said sample with a set of primers, each member of said set of primers comprising between 3 and 8 random bases and at least 8 essentially non-random bases;
   subjecting said sample to a first nucleic acid amplification reaction;
   providing said sample with at least one second primer comprising at least 8 bases essentially identical to said non-random bases;
   subjecting said sample to a second amplification reaction;
   detecting amplified nucleic acid in said sample, wherein the presence of amplified nucleic acid indicates said positive diagnosis and the absence of amplified nucleic acid indicates said negative diagnosis; and
   providing said positive or negative diagnosis to the subject.

23. The method according to claim 1, wherein said set of primers comprises SEQ ID NO:2.

24. A set of oligonucleotides, said set of oligonucleotides comprising SEQ ID NO:2.

25. A method for preferentially amplifying at least part of a viral nucleic acid, said method comprising:
   providing a sample comprising said viral nucleic acid;
   providing said sample with a set of oligonucleotides comprising SEQ ID NO:2;
   subjecting said sample to a nucleic acid amplification reaction; and
   detecting amplified viral nucleic acid in said sample.

26. A kit of parts for implementing a nucleic acid amplification reaction on a sample comprising nucleic acid, said kit of parts comprising:
   a set of primers comprising between 3 and 8 random bases, wherein said set of primers comprises SEQ ID NO:2.

* * * * *

(12) INTER PARTES REEXAMINATION CERTIFICATE (0020th)

United States Patent
Zhang et al.

(10) Number: US 6,808,888 C1
(45) Certificate Issued: Apr. 29, 2008

(54) UNIVERSAL NUCLEIC ACID AMPLIFICATION SYSTEM FOR NUCLEIC ACIDS IN A SAMPLE

(75) Inventors: Jing Zhang, St. Louis, MO (US); John Dekker, Beverwijk (NL); Antoinette C. van der Kuyl, Loosdrecht (NL); Jolanda Maas, Amsterdam (NL); Bob van Gemen, Almere (NL)

(73) Assignee: Primagen Holding B.V., Amsterdam (NL)

Reexamination Request:
No. 95/000,132, Mar. 3, 2006

Reexamination Certificate for:
Patent No.: 6,808,888
Issued: Oct. 26, 2004
Appl. No.: 10/192,786
Filed: Jul. 10, 2002

Related U.S. Application Data

(63) Continuation of application No. PCT/NL01/00020, filed on Jan. 15, 2001.

(51) Int. Cl.
*C12Q 1/68* (2006.01)
*C12Q 1/70* (2006.01)
*C12P 19/34* (2006.01)
*C12P 19/00* (2006.01)
*C07H 19/00* (2006.01)
*C07H 21/00* (2006.01)
*C07H 21/04* (2006.01)

(52) U.S. Cl. .................. 435/6; 435/91.1; 435/91.2; 435/7.1; 536/22.1; 536/23.1; 536/24.3; 536/24.31; 536/24.32; 536/24.33

(58) Field of Classification Search .................. None
See application file for complete search history.

(56) References Cited

U.S. PATENT DOCUMENTS

| 5,104,792 A | * | 4/1992 | Silver et al. | .................. 435/6 |
| 5,545,522 A | * | 8/1996 | Van Gelder et al. | ............ 435/6 |
| 5,731,171 A | * | 3/1998 | Bohlander | ................. 435/91.2 |
| 5,861,245 A | * | 1/1999 | McClelland et al. | ........... 435/6 |

FOREIGN PATENT DOCUMENTS

WO     WO 9730062 A1 * 8/1997

OTHER PUBLICATIONS

Grothues et al., Nucleic Acids Research, 21:1321–1322 (1993).*
Hamer et al., Prenat. Diagnos. 19:1193–1199 (1999).*
Telenius et al., Genomics 13:718–725 (1992).*
Bohlander et al., Genomics 13:1322–1324 (1992).*
Cheung et al., Proc. Natl. Acad. Sci. USA 93:14676–14679 (1996).*
Zheleznaya et al., Biochemistry (Moscow) 64:373–378 (1999).*

* cited by examiner

*Primary Examiner*—Bennett Celsa

(57) ABSTRACT

Methods for amplifying nucleic acid in a sample comprising providing the sample with a set of primers to enable synthesis of at least one nucleic acid strand complementary to at least part of the nucleic acid, wherein the set of primers comprises between 3–8 random bases, preferably clustered near the 3' end of each primer in said set of primers. The methods of the invention are useful, for example, for determining whether samples derived from humans, mammals, poultry, or fish comprise nucleic acid of a pathogen. The methods are further suited for typing the pathogen and typing particular variants of said pathogen. The methods are also suited for the elucidation of the gene expression profile or genetic profile of cells.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 14–15, 21 and 24–26 is confirmed.

Claims 1–13, 16–20 and 22–23 are cancelled.

* * * * *